United States Patent
Bohlmann et al.

(10) Patent No.: US 6,693,188 B2
(45) Date of Patent: Feb. 17, 2004

(54) N-ACETYL-D-GLUCOSAMINE AND PROCESS FOR PRODUCING N-ACETYL-D-GLUCOSAMINE

(75) Inventors: John Andrew Bohlmann, Ottumwa, IA (US); David O. Schisler, Oskaloosa, IA (US); Ki-Oh Hwang, Oskaloosa, IA (US); Joseph P. Henning, Eddyville, IA (US); James R. Trinkle, Bussey, IA (US); Todd Bryan Anderson, Oskaloosa, IA (US); James Donald Steinke, Oskaloosa, IA (US); Andrea Vanderhoff, Pella, IA (US)

(73) Assignee: Cargill Incorporated, Wayzata, MN (US)

( * ) Notice: Subject to any disclaimer, the term of this patent is extended or adjusted under 35 U.S.C. 154(b) by 0 days.

(21) Appl. No.: 09/924,865

(22) Filed: Aug. 8, 2001

(65) Prior Publication Data

US 2003/0073666 A1 Apr. 17, 2003

(51) Int. Cl.$^7$ .............. C07H 5/06; C07H 5/04; A61K 31/7008; C12P 19/28
(52) U.S. Cl. .......... 536/55.2; 536/55.3; 536/53; 514/62; 435/84
(58) Field of Search .............. 536/55.2, 55.3, 536/53; 514/62; 435/84

(56) References Cited

U.S. PATENT DOCUMENTS

| | | | |
|---|---|---|---|
| 2,040,879 A | 5/1936 | Rigby | |
| 3,232,836 A | 2/1966 | Carlozzi et al. | |
| 3,632,754 A | 1/1972 | Balassa | |
| 3,903,268 A | 9/1975 | Balassa | |
| 3,911,116 A | 10/1975 | Balassa | |
| 3,914,413 A | 10/1975 | Balassa | |
| 4,056,432 A | 11/1977 | Slagel et al. | |
| 4,282,351 A | 8/1981 | Muzzarelli | |
| 4,642,340 A | 2/1987 | Senin et al. | |
| 4,806,474 A | 2/1989 | Hershberger | |
| 4,948,881 A | 8/1990 | Naggi et al. | |
| 4,970,150 A | 11/1990 | Yaku et al. | |
| 4,983,304 A | 1/1991 | Tsugita et al. | |
| 5,219,749 A | 6/1993 | Bouriotis et al. | |
| 5,232,842 A | 8/1993 | Park et al. | |
| 5,262,310 A | 11/1993 | Karube et al. | |
| 5,702,939 A | 12/1997 | Fujishima et al. | |
| 5,730,876 A | 3/1998 | You et al. | |
| 5,843,923 A | 12/1998 | Schleck et al. | |
| 5,902,801 A | 5/1999 | Schleck et al. | |
| 5,905,035 A | 5/1999 | Okada et al. | |
| 5,985,644 A | 11/1999 | Roseman et al. | |
| 5,998,173 A | 12/1999 | Haynes et al. | |
| 6,117,851 A | 9/2000 | Sherman et al. | |
| 6,248,570 B1 | 6/2001 | Michon et al. | |
| 6,333,399 B1 | 12/2001 | Teslenko et al. | |

FOREIGN PATENT DOCUMENTS

| | | |
|---|---|---|
| EP | 0 885 954 A1 | 12/1998 |
| GB | 458839 | 12/1936 |
| GB | 785525 | 10/1957 |
| GB | 833264 | 4/1960 |
| GB | 896940 | 5/1962 |
| JP | 55012109 | 1/1980 |
| JP | 62070401 A2 | 3/1987 |
| JP | 63097633 A2 | 4/1988 |
| JP | 63225602 A2 | 9/1988 |
| JP | 2149335 A2 | 6/1990 |
| JP | 2180903 A2 | 7/1990 |
| JP | 2200196 A2 | 8/1990 |
| JP | 2229832 A2 | 9/1990 |
| JP | 2258740 A2 | 10/1990 |
| JP | 5068580 A2 | 10/1993 |
| JP | 7330808 A2 | 12/1995 |
| JP | 8-41106 A | 2/1996 |
| JP | 10297913 A2 | 11/1998 |
| WO | WO 98/42755 | 10/1998 |
| WO | WO 00/04182 | 1/2000 |

OTHER PUBLICATIONS

Domanski et al. (Journal of Bacteriolgy, Jul. 1968, p. 270–271.).*
Li et al. (Yaowu Shengwu Jishu (1999), 6 (3), 147–149) (abstract sent).*
Jackson et al. (Transactions of the British Mycological Society (1976) 66, Pt. 3, 463–71) (abstract sent).*
Stainer, R. et al., "The Microbial World", *Prentice–Hall, Inc.*, pp. 332–336 (1970).
Alonso, I. et al., "Determination of the Degree of Acetylation of Chitin and Chitosan by Thermal Analysis", *Journal of Thermal Analysis*, vol. 28, pp. 189–193 (1983).
Arcidiacono, S. et al., "Molecular Weight Distribution of Chitosan isolated from *Mucor rouxii* under Different Culture and Processing Conditions", *Biotechnology And Bioengineering*, vol. 39, pp. 281–286 (1992).
Bartnicki–Garcia, S., "Cell Wall Chemistry, Morphogenesis, and Taxonomy of Fungi", *Chemistry of Fungal Cell Wall* pp. 87–108 (1968).
Benjakul, S. et al., "Improvement of Deacetylation of Chitin from Black Tiger Shrimp (*Penaeus monodon*) Carapace and Shell", *ASEAN Food Journal*, vol. 9, No. 4, pp. 136–140 (1994).

(List continued on next page.)

*Primary Examiner*—Samuel Barts
*Assistant Examiner*—Michael C. Henry
(74) *Attorney, Agent, or Firm*—Paula Degrandis (57) ABSTRACT

The present invention is directed to N-acetyl-D-glucosamine obtained from microbial biomass, and to methods of obtaining N-acetyl-D-glucosamine from microbial biomass. In particular, the present invention is directed to the use of fungal biomass to create N-acetyl-D-glucosamine. The N-acetyl-D-glucosamine is efficiently obtained at high purity by degrading chitin in the fungal biomass to create N-acetyl-D-glucosamine.

15 Claims, 6 Drawing Sheets

OTHER PUBLICATIONS

Beri, R. et al., "Characterization of Chitosans via Coupled Size–Exclusion Chromatography and Multiple–Angle Laser Light–Scattering Technique", *Carbohydrate Research*, vol. 238, pp. 11–26 (1993).

Biermann, C., "Hydrolysis and Other Cleavage of Glycosidic Linkages", Chapter 3, pp. 29–41 (Date Unknown).

Carlson, T. et al., "Chitin/Chitosan Extraction from *A. Niger* Mycelium", *Cargill Central Research*, 16 pages (Aug. 1997).

"Chitin/Chitosan Specifications", *Biopolymer Engineering, Inc.*, http://www.biopolymer.com/spec.htm, 1 page (Date Printed Mar. 4, 1999).

Davies, D. et al., "Determination of the Degree of Acetylation of Chitin and Chitosan", *Methods in Enzymology*, vol. 161, Part B, pp. 442–446 (1988).

Deal, C. et al., "Nutraceuticals as Therapeutic Agents in Osteoarthritis. The Role of Glucosamine, Chondroitin Sulfate, and Collagen Hydrolysate", *Osteoarthritis*, vol. 25, No. 2, pp. 379–395 (May 1999).

Domszy, J. et al., "Evaluation of Infrared Spectroscopic Techniques for Analysing Chitosan", *Makromal. Chem.*, vol. 186, pp. 1671–1677 (1985).

Farkas, V., "Fungal Cell Walls: Their Structure, Biosynthesis and Biotechnological Aspects", *Acta Biotechnol.*, vol. 10, No. 3, pp. 225–238 (1990).

Ferrer, J., "Acid Hydrolysis of Shrimp–Shell Wastes and the Production of Single Cell Protein from the Hydrolysate", *Bioresource Technology*, vol. 57, pp. 55–60 (1996).

Fleet, G. et al., "17 Fungal Glucans—Structure and Metabolism", *Encyclopedia of Plant Physiology*, vol. 13B. New Series, pp. 416–440 (1981).

"The Fungal Cell", Chapter 2, pp. 22–39 (Date Unknown).

Gassner, G. et al., "Teichuronic Acid Reducing Terminal N–Acetylglucosamine Residue Linked by Phosphodiester to Peptidoglycan of *Micrococcus luteus*", *J. Bacteriol.*, vol. 172, No. 5, pp. 2273–2279 (May 1990).

"Glucosamine Hydrochloride", *Pharmacopeial Forum*, vol. 26, No. 5, pp. 14491450 (Sep.–Oct. 2000).

Gobin, P. et al., "Structural Chemistry of Fungal Polysaccharides", pp. 367–417 (1968).

Jacobson, R., "Berichte der Deutschen Chemischen Gesellschaft", pp. 21922200 (1898) (German).

Johnston, I., "The Composition of the Cell Wall of *Asperigillus niger*", *Biochem. J*, vol. 96, pp. 651–658 (1965).

Kimura, K. et al., "Determination of the Mode of Hydrolysis of Chitooligosaccharides by Chitosanase Derived from *Aspergillus Oryzae* by Thin Layer Chromatography", *Chemistry Letter*, pp. 223–226 (1992).

Kurita, K., "Controlled Functionalization of the Polysaccharide Chitin",*Prog. Polym. Sci.*, vol. 26, pp. 1921–1971 (2001).

Kurita, K. et al., "Studies on Chitin, 3, Preparation of Pure Chitin, Poly(N–acetyl–D–glucosamine), from the Water-Soluble Chitin", *Makromal. Chem.*, vol. 178, pp. 25952602 (1977).

Kurita, K. et al., "Studies on Chitin, 4, Evidence for Formation of Block and Random Copolymers of N–Acetyl–D-–glucosamine and D–Glucosamine by Hetero–and Homogeneous Hydrolyses", *Makromol. Chem.*, vol. 178, pp. 3197–3202 (1977).

Maghami, G. et al., "Evaluation of the Viscometric Constants for Chitosan", *Makromol. Chem.*, vol. 189, pp. 195–200 (1988).

Maitre, N. et al., "Primary T–Cell and Activated Macrophage Response Associated with Tumor Protection Using Peptide/Poly–N–Acetyl Glucosamine Vaccination", *Clinical Cancer Research*, vol. 5, pp. 1173–1182 (May 1999).

Mima, S. et al., "Highly Deacetylated Chitosan and Its Properties",*Journal of Applied Polymer Sciences*, vol. 28, pp. 1909–1917 (1983).

Muzzarelli, R. et al., Chelating, Film–Forming, and Coagulating Ability of the Citosan–Glucan Complex from *Aspergillus niger* Industrial Wastes, *Biotechnology and Bioengineering*, vol. XXII, pp. 885896 (1980).

Nanjo, F. et al., "Purification, Properties, and Transglycosylation Reaction of$\beta$–N–Acetylhexosaminidase from *Nocardia orientalis*", *Agric. Biol. Chem.*, vol. 54, No. 4, pp. 899–906 (1990).

Nanjo, F. et al., "Purification and Characterization of an Exo–$\beta$–D–glucosaminidase, a Novel Type of Enzyme, from *Nocardia orientalis*", *The Journal of Biological Chemistry*, vol. 265, No. 17, pp. 10088–10094 (Jun. 15, 1990).

Nanjo, F. et al., "Enzymatic Method for Determination of the Degree of Deacetylation of Chitosan", *Analytical Biochemistry*, vol. 193, pp. 164–167 (1991).

Nguyen, T. et al., "Composition of the Cell Walls of Several Yeast Species",*Abstract* vol. 50, No. 2, pp. 206–212 (1998).

Niola, F. et al., "A Rapid Method for the Determination of the Degree of N–acetylation of chitin–chitosan samples by acid hydrolysis and HPLC", *Carbohydrate Research*, vol. 238, pp. 1–9 (1993).

No, H. et al., "Preparation and Characterization of Chitin and Chitosan—A Review", *Journal of Aquatic Food Product Technology*, vol. 4, No. 2, pp. 27–51 (1995).

Nogawa, M. et al., "Purification and Characterization of Exo–$\beta$–D–Glucosaminidase from a Cellulolytic Fungas, *Trichoderma reesei* PC–3–7", *Appl. Environ. Microbiol.*, vol. 64, No. 3, pp, 890–895 (Mar. 1998).

Novikov, V. et al., "Synthesis of D(+)–Glucossamine Hydrochloride", *Russian Journal of Applied Chemistry*, vol. 70, No. 9, pp. 1467–1470 (1997).

Ottoy, M. et al., "Preparative and Analytical Size–exclusion Chromatography of Chitosans", *Carbohydrate Polymers*, vol. 31, pp. 253–261 (1996).

Pelletier, A. et al., "Chitin/Chitosan Transformation by Thermo–Mechano–Chemical Including Characterization by Enzymatic Depolymerization", *Biotechnology and Bioengineering*, vol. 36, pp. 310–315 (1990).

Rege, P. et al., "Chitosan Processing: Influence of Process Parameters During Acidic and Alkaline Hydrolysis and Effect of the Processing Sequence on the Resultant Chitosan's Properties", *Carbohydrate Research*, vol. 321, Nos. 3-4, pp. 235–245 (Oct. 15, 1999).

Roberts, G. et al., "Determination of the Viscomtric Constants for Chitosan", *Int. J. Biol.*, vol. 4, pp. 374–377 (Oct. 1982).

Rokem, J. et al., "Degradation of Fungal Cell Walls Taking into Consideration the Polysaccharide Composition", *Enzyme Microb. Technol.*, vol. 8, No. 10, pp. 588–592 (Oct. 1986) (Abstract).

Ruiz–Herrera, J., "Chemical Components of the Cell Wall of Aspergillus Species", *Archives of Biochemistry and Biophysics*, vol. 122, pp. 118–125 (1967).

Sabnis, S. et al., "Improved Infrared Spectroscopic Method for the Analysis of Degree of N–decacetylation of Chitosan", *Polymer Bulletin*, vol. 39, pp. 61–71 (1997).

Sakai, K. et al., "Purification and Hydrolytic Action of a Chitosanase from *Nocardia orientalis*", *Biochimica et Biophysica Acta.*, vol. 1079, pp. 65–72 (1991).

Sannan, T. et al., "Studies on Chitin, 2, Effect of Deacetylation on Solubility", *Makromol. Chem.*, vol. 177, pp. 3589–3600 (1976).

Shahidi, F. et al., "Food Applications of Chitin and Chitosans", *Trends in Food Science & Technology*, vol. 10, pp. 37–51 (1999).

Shu, C–K, "Degradation Products Formed from Glucosamine in Water", *J. Agric. Food. Chem.*, vol. 46, pp. 1129–1131 (1998).

Stagg, C. et al., The Characterization of a Chitin–Associated D–Glucan from the Cell Walls of *Aspergillus Niger*, vol. 320, pp. 64–72 (1973).

Tan, S. et al., "The Degree of Deacetylation of Chitosan: Advocating the First Derivative UV–spectrophotometry Method of Determination", *Talanta,* vol. 45, pp. 713–719 (1998).

Wessels, J. et al., "15 Fungal Cell Walls: A Survey", *Plant Carbohydrates II, Extracellular Carbohydrates,* pp. 352–394 (1981).

Wu, A. et al., "Determination of Molecular–Weight Distribution of Chitosan by High–performance Liquid Chromatography", *Journal of Chromatography,* vol. 128, pp. 87–99 (1976).

Jackson et al. (Transactions of the British Mycological Society (1976) 66, Pt. 3, 463–71).

Atrih, A. et al., "Analysis of Peptidoglycan Structure from Vegetative Cells of *Bacillus subtilis* 168 and Role of PBP 5 in Peptidoglycan Maturation", *Journal of Bacteriology,* vol. 181, No. 13, pp. 39563966 (Jul. 1999).

* cited by examiner

N-ACETYL-D-GLUCOSAMINE AND PROCESS FOR PRODUCING N-ACETYL-D-GLUCOSAMINE

FIELD OF THE INVENTION

The present invention is directed to N-Acetyl-D-Glucosamine and methods of making N-Acetyl-D-Glucosamine.

BACKGROUND

Chitin is a natural polysaccharide present in various marine and terrestrial organisms, including crustacea, insects, mollusks, and microorganisms, such as fungi. The structure of chitin is that of an unbranched polymer of 2-acetoamido-2-deoxy-D-glucose (also known as poly (N-acetyl-D-glucosamine)), and can be represented by the general repeating structure:

Chitin is typically an amorphous solid that is largely insoluble in water, dilute acids, and alkali. Although chitin has many uses, it can also be degraded to form other useful materials, such as carbohydrates, one of which is the amino sugar N-acetyl-D-glucosamine (NAG). N-acetyl-D-glucosamine typically includes a single glucosamine unit, but can also include small amounts of short oligomers, such as chitobiose or chitotriose, that have two and three glucosamine units, respectively. N-acetyl-D-glucosamine can be used for various applications, including as a food additive and in pharmaceutical compositions.

The most common source of chitin for use in making N-acetyl-D-glucosamine is shellfish (such as shrimp) biomass. Unfortunately, limitations exist with the recovery of N-acetyl-D-glucosamine from shellfish biomass. One problem with recovering N-acetyl-D-glucosamine from shellfish is that it is very difficult to obtain uniform shellfish biomass. The uniformity problems occur in part because shellfish often vary by size, age, and species; are grown under varied environmental conditions; and are gathered from diverse locations. This lack of uniformity makes it difficult to precisely process shellfish biomass. In addition, some quality control issues can arise due to the fact that N-acetyl-D-glucosamine obtained from crustacea can have a high ash content and can contain heavy metals that are concentrated in the crustacea from their aquatic environment. A further problem with N-acetyl-D-glucosamine derived from harvested crustacea is that it has the potential to include undesired proteins and allergens.

Therefore, a need exists for an improved N-acetyl-D-glucosamine material that is obtained utilizing a non-shellfish chitin source.

SUMMARY OF THE INVENTION

The present invention is directed to N-acetyl-D-glucosamine obtained from microbial biomass, and to methods of obtaining N-acetyl-D-glucosamine from microbial biomass. In particular, the present invention is directed to the use of fungal biomass to obtain N-acetyl-D-glucosamine. The N-acetyl-D-glucosamine is efficiently obtained at high purity by degrading chitin in the biomass to create N-acetyl-D-glucosamine.

The fungal biomass generally contains a significant amount of glucan intermixed with the chitin. Glucan is a high molecular weight polymer of glucose and is derived from the cell wall of microbial biomass. Glucan can include linkages that are exclusively beta linkages, exclusively alpha linkages, or a mixture of alpha and beta linkages. The glucan components of the fungal biomass bind and immobilize the chitin materials, and generally make the chitin unavailable for efficient degradation into N-acetyl-D-glucosamine. The present invention overcomes the problems associated with the presence of glucan components by degrading the glucan sufficiently to gain chemical access to the chitin components, which are subsequently degraded to form N-acetyl-D-glucosamine.

The methods of recovering N-acetyl-D-glucosamine generally include providing fungal biomass containing chitin and glucan; degrading at least a portion of the glucan; and degrading at least a portion of the chitin to produce N-acetyl-D-glucosamine. In one implementation of the invention the chitin and glucan are enzymatically degraded, while in other implementations the chitin and glucan are chemically degraded.

The biomass used to form the N-acetyl-D-glucosamine of the invention typically is a fungal biomass that has at least 5 weight percent chitin and at least 5 weight percent glucan on a dry basis before degradation, and even more typically has at least 15 weight percent chitin and 50 weight percent glucan on a dry basis before degradation.

Various fungal biomass sources can be used, including fungal biomass derived from Aspergillus sp., Penicillium sp., Absidium sp., Lactarius sp., Mucor sp., Saccharomyces sp., Candida sp. or combinations thereof. As used herein, "sp." refers to either singular "specie" or plural "species". Suitable specific microbial biomasses include, without limitation, *Aspergillus niger, Aspergillus terreus, Aspergillus oryzae, Lactarius vellereus, Mucor rouxii, Penicillium chrysogenum, Penicillium notatum, Saccharomyces cerevisiae*; and in particular, *Candida guillermondi, Aspergillus niger*, and *Aspergillus terreus*. Generally the biomass is recovered from a commercial fermentation reaction, including the commercial production of organic acids, such as citric acid and itaconic acid. As use herein, the term microbial when used to describe the fungal biomass source does not include phyto-plankton and crustaceans or mollusks, which differ significantly in composition and properties from fungal biomass.

In one implementation of the invention the chitin and glucan components of the fungal biomass are degraded by enzymes. The enzymes are typically microorganism-derived. The enzymes can be added to the fungal biomass in the presence of the microorganisms from which they are derived, which has the advantage of avoiding the step of separating the enzymes from their source organisms. Inclusion of the source microorganisms can also be advantageous in implementations where the microorganisms continue to create enzymes after having been added to the fungal biomass. In other implementations the enzymes are separated from their source microorganisms (such as by filtration or centrifugation) and subsequently added to the fungal biomass.

Suitable enzymes for degrading the chitin and glucan include chitinases, β-N-acetyl-glucosaminidases, and glucanases. The enzymes are generally secreted from eucaryotic or prokaryotic microorganisms. Suitable eucaryotic organisms include those from the Trichoderma genus, including, for example, *Trichoderma harizianum* and *Trichoderma reesei*. Suitable prokaryotic organisms include those from the Serratia genus, the Streptomyces genus, and the Nocardia genus. Example prokaryotic organisms include *Serratia marcesens, Streptomyces griseus*, and *Nocardia orientalis*. Glucanase enzymes are particularly advantageous in order to degrade the glucan component of the fungal biomass. These glucanases should be present at relatively high concentrations in typical implementations of the invention.

In general it is not necessary to subject the fungal biomass to extensive physical or chemical pretreatments prior to processing to create N-acetyl-D-glucosamine. Thus, it is usually not necessary to grind the fungal biomass or to pretreat it with an organic solvent. Such steps are normally not required, but they can optionally be performed in some implementations of the invention. When enzymes are used to degrade the chitin and glucan, the degradation reaction is usually maintained at a pH of 4.0 to 6.0 and a temperature of 20° to 45° C. Higher temperatures are generally advantageous, but the temperatures must be low enough to keep the enzymes from degrading.

Despite the high levels of glucan present in the fungal biomass, the resulting N-acetyl-D-glucosamine is generally of high purity. Typically the resulting N-acetyl-D-glucosamine makes up at least 85 percent of the chitin-derived carbohydrates from the fungal biomass.

The above summary of the present invention is not intended to describe each disclosed embodiment of the present invention. This is the purpose of the detailed description and claims that follow.

BRIEF DESCRIPTION OF THE DRAWINGS

Other aspects and advantages will become apparent upon reading the following detailed description and upon reference to the drawings in which.

While the disclosure is susceptible to various modifications and alternative forms, specifics are shown by way of example and are described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION OF THE INVENTION

Specific aspects of the N-acetyl-D-glucosamine, biomass, and method of the invention are described below. The present invention is directed to N-acetyl-D-glucosamine obtained from microbial biomass, and to methods of obtaining N-acetyl-D-glucosamine from microbial biomass. In particular, the present invention is directed to the use of fungal biomass to create N-acetyl-D-glucosamine. The fungal biomass generally contains a significant amount (at least 15%) of glucan intermixed with the chitin.

The glucan components of the fungal biomass retain and immobilize the chitin materials, and generally make the chitin unavailable for easy degradation into N-acetyl-D-glucosamine. The retention and immobilization of the chitin is particularly problematic because it can interfere with rapid, efficient production of N-acetyl-D-glucosamine by either slowing down the production of N-acetyl-D-glucosamine or by requiring the use of harsh reaction conditions that break down the glucan but also simultaneously degrade the N-acetyl-D-glucosamine. Thus, it is necessary to degrade the glucan without losing an excessive amount of N-acetyl-D-glucosamine in the process.

The present invention overcomes the problems associated with the presence of glucan components by degrading the glucan sufficiently to gain chemical access to the chitin components, which are subsequently degraded to form N-acetyl-D-glucosamine, without excessively degrading the N-acetyl-D-glucosamine that is produced. As used herein, "degradation" refers to sufficient change in the glucan to permit transforming the adjacent chitin into N-acetyl-D-glucosamine.

The invention generally includes providing fungal biomass containing chitin and glucan, degrading at least a portion of the glucan, and degrading at least a portion of the chitin to produce N-acetyl-D-glucosamine. In one implementation of the invention the chitin and glucan are enzymatically degraded, while in other implementations the chitin and glucan are chemically degraded.

Chitin-Containing Biomass

The present invention is directed to N-acetyl-D-glucosamine recovered from microbial biomass, primarily fungal biomass, including yeast and filamentous fungi. The biomass used to form the N-acetyl-D-glucosamine of the invention typically is a fungal biomass that has at least 5 weight percent chitin and at least 5 weight percent glucan on a dry basis before degradation, and even more typically has at least 15 weight percent chitin and 50 weight percent glucan on a dry basis before degradation. Most of the fungal biomass has 15–20 wt. % chitin; about 60 wt. % glucan; 15–20 wt. % protein; and a small percentage of lipids, mannan, galactan, etc. The remaining unaccounted for materials can include nucleic acids, phosphatidic acid, and lipid substituents such as choline, ethanolamine, serine, and inositol. After the biomass is processed using the method of the invention, the composition is typically about 85 wt. % N-acetyl-D-glucosamine and 15 wt. % or less glucan.

Various fungal biomass sources can be used, including fungal biomass derived from Aspergillus sp., Penicillium sp., Mucor sp., Absidium sp., Lactarius sp., Saccharomyces sp., Candida sp. or combinations thereof. Suitable microbial biomasses include *Aspergillus niger, Aspergillus terreus, Aspergillus oryzae, Lactarius vellereus, Mucor rouxii, Penicillium chrysogenum, Penicillium notatum, Saccharomyces cerevisiae*; and in particular *Candida guillermondi, Aspergillus niger*, and *Aspergillus terreus*. Generally the biomass is recovered from a commercial fermentation reaction, including the commercial production of organic acids, such as citric acid or itaconic acid. Although it is possible to generate biomass solely for the purpose of obtaining N-acetyl-D-glucosamine, the biomass most often is a by-product of other production processes. For example, citric-acid fermentation facilities use fungi to create citric acid. Traditionally, the fungal biomass from citric-acid fermentation has been discarded or used as fuel, feed, or fertilizer. The present invention allows extraction of high quality N-acetyl-D-glucosamine from this fungal biomass.

Biomass suitable for use in the present invention includes most types of chitin-containing microbial biomass, and in particular fungal biomass. The invention is particularly well suited to uses where the chitin levels exceed 5 percent of the dry biomass weight. Such biomass usually has between 5 and 25 percent chitin, and typically from 10 to 20 percent chitin, based upon dry weight of the biomass. In order to prepare the highest quality N-acetyl-D-glucosamine, it is sometimes desirable that the microbial biomass be produced in a substantially controlled manner having relatively uniform temperature and nutrient levels during the growth of the biomass.

Method of Obtaining N-acetyl-D-glucosamine from Chitin-Containing Fungal Biomass The present invention is also directed, in part, to improved methods of producing N-acetyl-D-glucosamine from chitin-containing biomass. In one implementation of the invention the chitin and glucan components of the fungal biomass are degraded by enzymes. The enzymes are typically microorganism-derived. The enzymes may be added to the fungal biomass in the presence of the microorganisms from which they are derived, which has the advantages of avoiding the step of separating the enzymes from their source organisms. Inclusion of the source microorganisms can also be advantageous in implementations where the microorganisms continue to create enzymes after having been added to the fungal biomass. In other implementations the enzymes are separated from their source microorganisms (such as by filtration or centrifugation) and subsequently added to the fungal biomass.

Suitable enzymes for degrading the chitin and glucan include chitinases, β-n-acetyl-glucosaminidases, and glucanases. The enzymes are typically secreted from a eucaryotic microorganism, such as an organism from the Trichoderma genus, including, for example, *Trichoderma harizianum* and *Trichoderma reesei*.

In general it is not necessary to subject the fungal biomass to extensive physical or chemical pretreatments prior to processing to create N-acetyl-D-glucosamine. Thus, it usually is not necessary to grind the fungal biomass or to pretreat it with an organic solvent. Although such steps are normally not required, they can optionally be performed in some implementations of the invention. When enzymes are used to degrade the chitin and glucan, the degradation reaction is usually maintained at a pH of 4.0 to 6.0 and a temperature of 20° to 45° C.

In alternative implementations of the invention N-acetyl-D-glucosamine is formed by chemical degradation of the chitin and glucan components of fungal biomass. Generally the chemical degradation can be performed by hydrolysis using a strong acid, such as hydrochloric acid. The processing temperature and volume of acid added to the fungal biomass should be selected such that it is great enough to produce N-acetyl-D-glucosamine without degrading the N-acetyl-D-glucosamine produced.

Higher temperatures and acid concentrations correspond to better N-acetyl-D-glucosamine production, but when temperatures and acid concentration get too high the N-acetyl-D-glucosamine that is produced can be simultaneously destroyed. Therefore, the temperature and acid concentration must be high enough to sufficiently degrade the chitin and glucan to produce N-acetyl-D-glucosamine, without being so high that the N-acetyl-D-glucosamine is destroyed. Suitable reaction conditions include, for example, approximately 20 percent HCl at 60° C. Other suitable ranges of reaction conditions include from about 10 to 36 percent HCl, even more typically 15 to 36 percent HCl. Suitable temperatures include from about 20° to 100° C., more typically from about 40° to 80° C.

N-acetyl-D-glucosamine

Despite the high levels of glucan present in the biomass, typically the resulting N-acetyl-D-glucosamine makes up at least 85 percent of the chitin-derived carbohydrates from the fungal biomass. Generally the N-acetyl-D-glucosamine composition contains a total of less than 15 weight percent glucan and glucan derivatives. These other glucan derivatives include, for example, glucose, maltose, and other glucose-based oligosaccharides.

The improved N-acetyl-D-glucosamine can be advantageously used in various applications. These applications include pharmaceuticals, general medical uses, nutritional and dietary products, and various other industrial and consumer products and processes. Various other applications and uses for the N-acetyl-D-glucosamine are also appropriate.

Example Methods of Obtaining N-acetyl-D-glucosamine

The following examples are provided to illustrate methods of making N-acetyl-D-glucosamine from fungal biomass. In the first example N-acetyl-D-glucosamine is formed using purified or isolated enzymes, in the second example N-acetyl-D-glucosamine is formed using a mixture of enzymes and enzyme producing organisms, and in the third example, N-acetyl-D-glucosamine is formed using a strong acid.

I. N-acetyl-D-glucosamine Produced Using Isolated Enzymes

In this first example N-acetyl-D-glucosamine was produced using *Aspergillus niger* fungal biomass generated from citric acid production. Enzymes isolated by filtering or centrifuging from their microbial sources (*T. harzianum* or *T. reesei*) were used to degrade the fungal biomass.

The fungal biomass source was prepared by pretreating with a number of reagents to degrade proteins and other contaminants, as well as to initiate degradation of the chitin and glucan. Specifically, 100 grams of citric acid biomass was added to a liter beaker. The 100 grams of *Aspergillus niger* biomass was used as it was received from a citric acid production facility. The biomass contained about 15 to 20 percent dry solids at the time of measurement. Therefore approximately 15 to 20 grams of mycelial citric acid biomass was used on a dry weight basis to a flask to contain one liter of media.

About one liter of water was added to the biomass. To this the following were added in the given order while mixing with a magnetic stirrer between 20° and 40° C. 2.79 grams of ammonium sulfate $((NH_4)_2SO_4)$ and 2.0 grams of monopotassium phosphate $(KH_2PO_4)$, 15.14 grams of sodium dihydrogen phosphate dihydrate $(NaH_2PO_4 \cdot 2\ H_2O)$, 0.3 grams of magnesium sulfate heptahydrate $(MgSO_4 \cdot 7\ H_2O)$, 19.94 grams of citric acid, 1.0 grams of peptone, and 0.59 grams of urea. Small amounts of additional ingredients were added, including 0.005 grams of iron sulfate heptahydrate $(FeSO_4 \cdot 7\ H_2O)$, 0.016 grams of manganese sulfate monohydrate $(MnSO_4 \cdot H_2O)$, 0.014 grams of zinc sulfate heptahydrate $(ZnSO_4 \cdot 7H_2O)$, and 0.02 grams of calcium chloride dihydrate $(CaCl_2 \cdot 2H_2O)$. While continuing to mix the solution, the pH of the media was adjusted to 5.5 with drop-wise additions of 50 percent potassium hydroxide (KOH). The media was divided into 120 ml quantities in 500 ml baffled flasks, and then sterilized.

Commercial enzymes were subsequently added to the pretreated fungal biomass upon sufficient cooling of the media. The consistency of the enzymes available commercially varies in reference to the unit activity. The following enzymes were used and aseptically transferred to the substrate:

Enzyme 1: Sigma L-1412 Lysing enzyme, containing 140 units per gram of chitinase, 0.728 units per gram of protease, and 1.54 units per gram of cellulase. 0.1 grams was added to the treatment tube, equivalent to 14 units of chitinase, 0.073 units of protease, and 0.154 units of cellulase;

Enzyme 2: Sigma C-6137 Chitinase enzyme, containing from 200 to 600 units per gram of chitinase (where one unit will liberate 1.0 mg of N-acetyl-D-glucosamine from chitin per hour at a pH of 6.0 and a temperature of 25° C in combination with β-N-acetyl glucosaminidase (also known as N-acetyl-D-glucosaminease) in a 2 hour assay). 0.001 grams of the enzyme was added to the treatment tube, equivalent to approximately 200 units of chitinase.

Enzyme 3: Sigma A-3189 β-N-acetyl glucosaminidase, containing from 50 to 150 units per milligram divided between 0.5% β-galactosidase and β-xylosidase and 2% alpha-galactosamine. Thus, one unit will hydrolyze 1.0 micromole of p-nitrophenyl N-acetyl-β-D-glucosaminide per minute at a pH of 4 at 25° C. to liberate terminal β-linked N-acetyl glucosamine and N-acetyl galactosamine from various substrates. Approximately five units of the β-N-acetyl glucosaminidase was added in the amount of a 0.1 ml solution to the treatment tube.

The lysing enzyme and the chitinase enzyme were hydrated with 0.1 milliliter of cold reagent buffer before being added to the 8.3 ml substrate (citric biomass media) tube at 25° C. All transfers of the buffer to the enzyme and enzyme to the substrate tube were done in an aseptic manner to decrease the possibility of airborne contamination. The reagent was a potassium phosphate buffer including the following: 200 mM potassium phosphate (2.72 grams per 100 milliliter), 2 mM calcium chloride (0.029 grams per 100 milliliter), dilute to 100 ml with de-ionized $H_2O$ and adjust the pH to 6.0 using 1M KOH. The buffer was autoclaved and stored at room temperature. Upon use for hydration, the buffer was chilled and kept on ice until used for hydration.

The N-acetyl-D-glucosaminidase was added directly to the reaction tube without mixing the buffer because it was already in a suspended form. Upon addition of the enzymes to the substrate tube, the tubes were immediately transferred into a glass beaker, which was placed in a 28° C. shaking water bath (at 180 rpm).

Samples were taken from the tube at 24 hours, 72 hours, and 96 hours by collecting approximately 1.5 milliliters of the sample, which was filtered undiluted with a 0.45 micrometer filter, and immediately analyzed for N-acetyl-D-glucosamine on a high pressure liquid chromatograph. The lysing enzyme alone and a combination of the chitinase and N-acetyl-D-glucosaminidase were used as the two treatments on the citric biomass media. The combination of the two enzymes resulted in 4.04 g/L N-acetyl-D-glucosamine at 72 hours (as shown in Table 1 and FIG. 1).

TABLE 1

Figure 1:
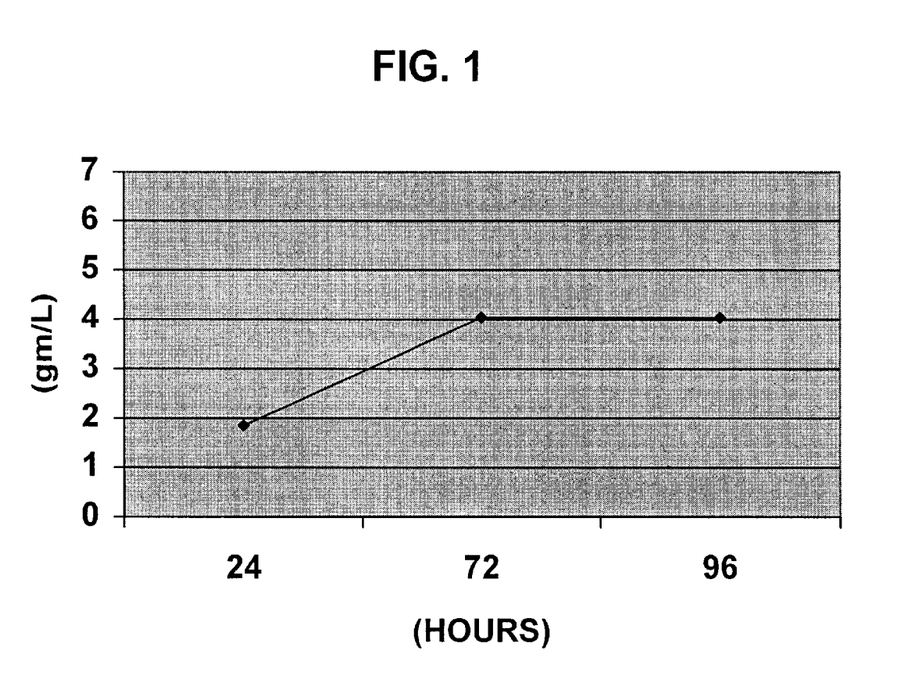
FIG. 1 is chart depicting N-acetyl-D-glucosamine production from fungal biomass using isolated enzymes to degrade the chitin and glucan.

| Hours | N-acetyl-D-glucosamine (g/L) |
|---|---|
| 24 | 1.85 |
| 72 | 4.04 |
| 96 | 4.04 |

N-acetyl-D-glucosamine Produced Using *Trichoderma harzianum* and *Trichoderma reesei*.

100 grams of citric biomass (containing about 15 to 20 percent by weight dry biomass) was placed in a 1 liter container. The pH of the biomass was adjusted to pH 5.5 with KOH, and sterilized in 120 ml amounts in 500 ml baffled flasks. The following ingredients were then added to the citric acid biomass in the following order while mixing with a magnetic stirrer: 2.79 grams of $(NH_4)_2SO_4$, 2.0 grams of $KH_2PO_4$, 15.14 grams of $NaH_2PO_4.2\ H_2O$ 0.3 grams of $MgSO_4.7\ H_2O$, 19.94 grams of citric acid, 1.0 grams of peptone, 0.59 grams of urea, 0.005 grams of $FeSO_4.7\ H_2O$, 0.016 grams of $MnSO_4.H_2O$, 0.014 grams of $ZnSO_4.7H_2O$, and 0.02 grams of $CaCl_2.2H_2O$. While mixing, the pH was adjusted to pH 5.5 with dropwise additions of 50 percent KOH, and sterilized in 120 ml amounts in 500 ml baffled flasks.

Upon cooling, the flasks were inoculated with 2 ml of *Trichoderma harzianum* and *Trichoderma reesei* (ATCC 66589) from a PDA slant hydrated with 1% Tween or a phosphate buffer used to hydrate the Trichoderma spores. The slants were hydrated with either Tween or buffer for approximately 5 minutes at room temperature prior to aseptically dispensing 2 ml of the hydrated spores into the 120 ml of media. The flasks were incubated at 28° C. in a rotary shaker at 180 rpm for 216 hours prior to transfer into the biomass. During this incubation period samples were taken every 24–48 hours for analysis of N-acetyl-D-glucosamine production. The example achieved 0.19 g/L at 212 hours in the first trial and achieved 0.22 g/L at 212 hours in the second trial as shown in Table 2 and FIG. 2.

TABLE 2

Figure 2:
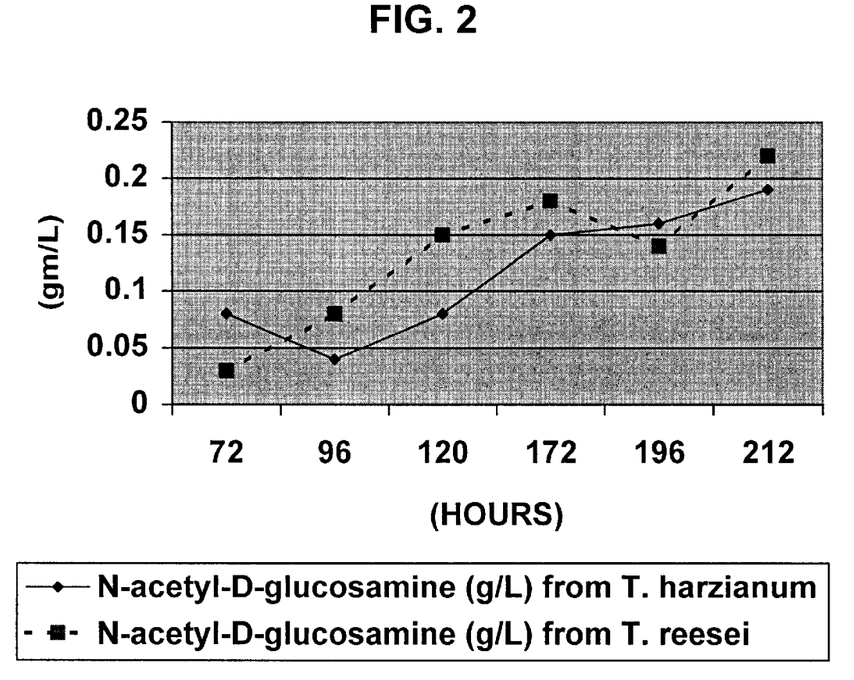
FIG. 2 is chart depicting N-acetyl-D-glucosamine production from fungal biomass using enzymes added in the presence of microorganisms to degrade the chitin and glucan.

| Hours | N-acetyl-D-glucosamine (g/L) from *T. harzianum* | N-acetyl-D-glucosamine (g/L) from *T. reesei* |
|---|---|---|
| 72 | 0.08 | 0.03 |
| 96 | 0.04 | 0.08 |
| 120 | 0.08 | 0.15 |
| 172 | 0.15 | 0.18 |
| 196 | 0.16 | 0.14 |
| 212 | 0.19 | 0.22 |

III. N-acetyl-D-glucosamine Produced Using Hydrochloric Acid

This example used chemical hydrolysis to produce N-acetyl-D-glucosamine from citric acid biomass (*Aspergillus niger*). Approximately 500 grams of biomass that had been previously treated with 2 percent sodium hydroxide (to remove proteins) was placed in a three-neck reactor flask. Hydrochloric acid and deionized water was added to adjust the acid concentration and biomass concentration to a desired value. The reactor was subsequently heated to 60° to 90° C., and samples drawn at 30 minute intervals for 6 to 7 hours. These samples were immediately analyzed for N-acetyl-D-glucosamine and glucosamine using a high pressure liquid chromatograph.

The results indicate that N-acetyl-D-glucosamine formation was favored under the conditions of 20 percent hydrochloric acid and 60° C. At these conditions up to 6.42 grams of N-acetyl-D-glucosamine were observed. It may also be seen that N-acetyl-D-glucosamine is kinetically favored due to the much lower rate of N-acetyl-D-glucosamine disappearance in the reactor vessel under these conditions compared to those at 90° C. Low hydrochloric acid levels (2 percent) showed little or no N-acetyl-D-glucosamine formation at 60° and 90° C.

Figure 3:
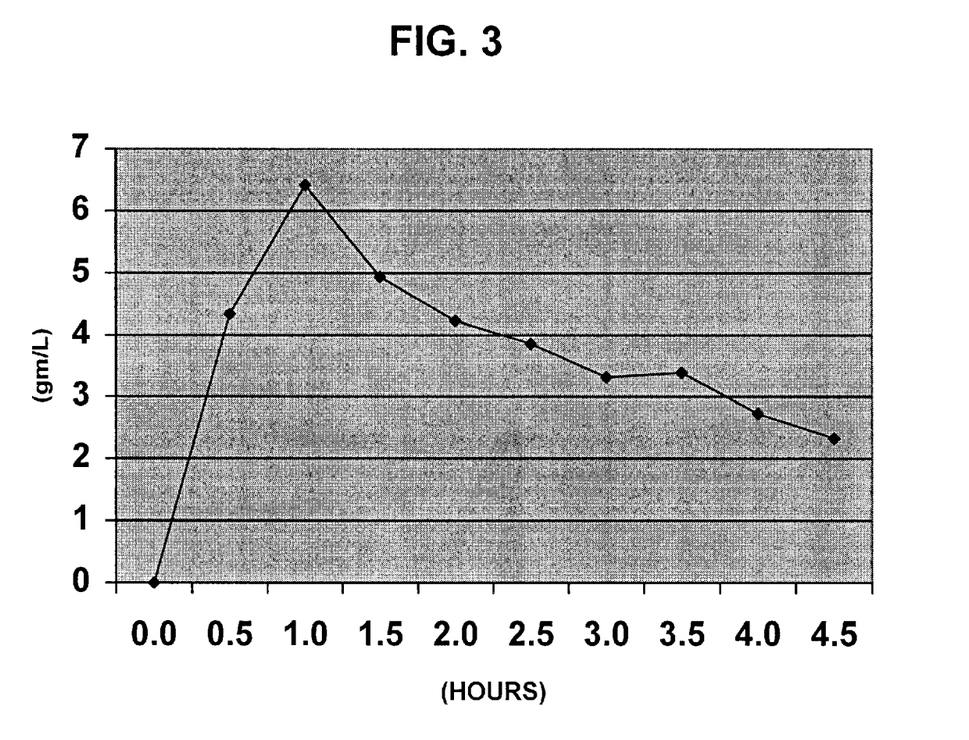
FIG. 3 is first chart depicting N-acetyl-D-glucosamine production from fungal biomass using chemical degradation of the chitin and glucan.

As indicated below in Table 3 and in FIG. 3, significant N-acetyl-D-glucosamine formation occurred at 20% HCl and 60° C.

TABLE 3

| Hours | N-acetyl-D-glucosamine (g/L) |
|---|---|
| 0 | 0 |
| 0.5 | 4.34 |
| 1.0 | 6.42 |
| 1.5 | 4.94 |
| 2.0 | 4.23 |
| 2.5 | 3.86 |
| 3.0 | 3.32 |
| 3.5 | 3.39 |
| 4.0 | 2.73 |
| 4.5 | 2.33 |

Figure 4:
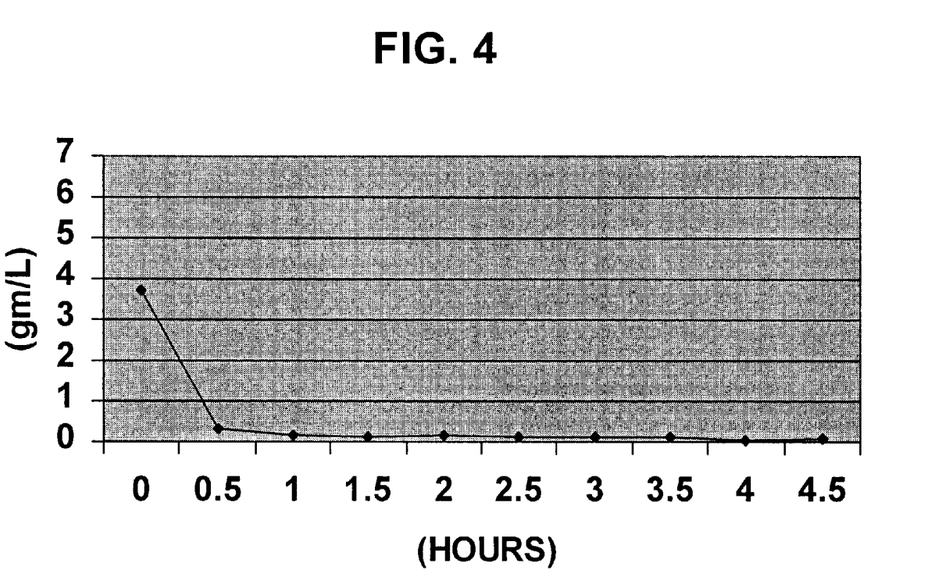
FIG. 4 is second chart depicting N-acetyl-D-glucosamine production from fungal biomass using chemical degradation of the chitin and glucan.

As indicated below in Table 4 and in FIG. 4, there was significant rapid production of N-acetyl-D-glucosamine from a mixture containing 20% HCl at 90° C., but this N-acetyl-D-glucosamine rapidly degraded and was lost from the solution.

TABLE 4

| Hours | N-acetyl-D-glucosamine (g/L) |
|---|---|
| 0 | 3.73 |
| 0.5 | 0.32 |
| 1.0 | 0.16 |
| 1.5 | 0.13 |
| 2.0 | 0.14 |
| 2.5 | 0.11 |
| 3.0 | 0.11 |
| 3.5 | 0.12 |
| 4.0 | 0.05 |
| 4.5 | 0.09 |

Figure 5:
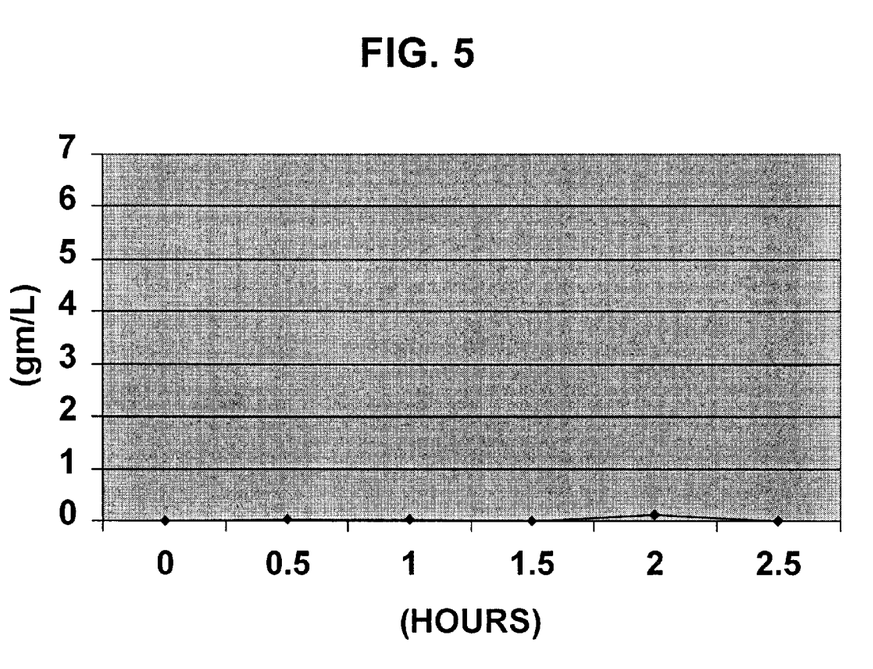
FIG. 5 is third chart depicting N-acetyl-D-glucosamine production from fungal biomass using chemical degradation of the chitin and glucan.

As indicated below in Table 5 and in FIG. 5, no significant amounts of N-acetyl-D-glucosamine were formed with 2% HCl solutions at 60° C.

TABLE 5

| Hours | N-acetyl-D-glucosamine (g/L) |
|---|---|
| 0 | 0.01 |
| 0.5 | 0.02 |
| 1.0 | 0.02 |
| 1.5 | 0.0 |
| 2.0 | 0.11 |
| 2.5 | 0.01 |

Figure 6:
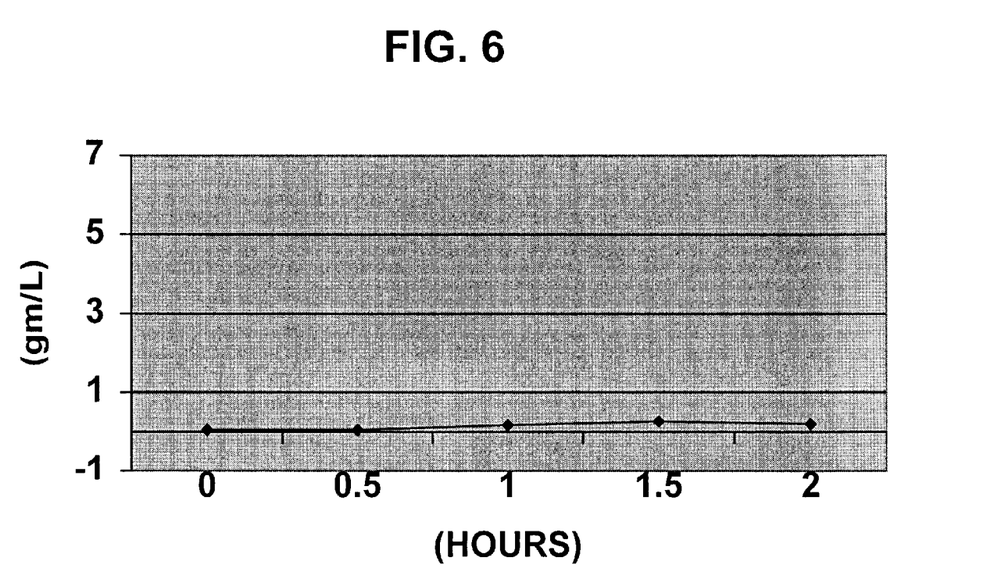
FIG. 6 is fourth chart depicting N-acetyl-D-glucosamine production from fungal biomass using chemical degradation of the chitin and glucan.

As indicated below in Table 6 and in FIG. 6, no significant amounts of N-acetyl-D-glucosamine were formed with 2% HCl solutions at 90° C.

TABLE 6

| Hours | N-acetyl-D-glucosamine (g/L) |
|---|---|
| 0 | 0.05 |
| 0.5 | 0.05 |

TABLE 6-continued

| Hours | N-acetyl-D-glucosamine (g/L) |
|---|---|
| 1.0 | 0.17 |
| 1.5 | 0.27 |
| 2.0 | 0.2 |

The above specification, examples and data provide a description of the compositions and methods of the invention. Since many embodiments of the invention can be made without departing from the spirit and scope of the invention, the invention resides in the following claims.

We claim:

1. A method of producing N-acetyl-D-glucosamine from fungal biomass, the method comprising:

a. providing fungal biomass containing chitin and glucan;

b. degrading at least a portion of the glucan with enzymes in the presence of the microorganisms that produce the enzymes; and c. degrading at least a portion of the chitin to produce N-acetyl-D-glucosamine with enzymes in the presence of the microorganisms that produce the enzymes.

2. The method of producing N-acetyl-D-glucosamine according to claim 1, wherein the fungal biomass before being degraded has at least 5 weight percent chitin and at least 5 weight percent glucan on a dry basis.

3. The method of producing N-acetyl-D-glucosanlifle according to claim 1, wherein the fungal biomass before being degraded has at least 15 weight percent chitin and 50 weight percent glucan on a dry basis.

4. The method of producing N-acetyl-D-glucosamine according to claim 1, wherein the resulting N-acetyl-D-glucosamine comprises at least 85 percent of all carbohydrates derived from the fungal biomass.

5. The method of producing N-acetyl-D-glucosamine according to claim 1, wherein at least 10 percent of the chitin is degraded to produce N-acetyl-D-glucosamine.

6. The method of producing N-acetyl-D-glucosamine according to claim 1, wherein at least 50 percent of the glucan is degraded.

7. The method of producing N-acetyl-D-glucosamine according to claim 1, wherein the fungal biomass is derived from Aspergillus sp., Penicillium sp., Mucor sp., Absidium sp., Lactarius sp., Saccharomyces sp., Candida sp. or combinations thereof.

8. The method of producing N-acetyl-D-glucosamine according to claim 1, wherein the fungal biomass contains at least 1 part glucan per part chitin.

9. The method of producing N-acetyl-D-glucosamine according to claim 1, wherein the chitin and glucan are enzymatically degraded by a chitinase, a beta-n-acetyl-glucosaminidase, and a glucanase.

10. A method of producing N-acetyl-D-glucosamine from fungal biomass, the method comprising:

a. providing fungal biomass containing chitin and glucan;

b. degrading at least a portion of the glucan; and c. degrading at least a portion of the chitin to produce N-acetyl-D-glucosamine, wherein the chitin and glucan are enzymatically degraded by a chitinase, a beta-n-acetyl-glucosaminidase, and a glucanase, and wherein the enzymes are secreted from a eucaryotic microorganism.

11. The method of producing N-acetyl-D-glucosamine according to claim 10, wherein the eucaryotic microorganism is selected from a microorganism of the Trichoderma genus.

12. The method of producing N-acetyl-D-glucosamine according to claim 11, wherein the eucaryotic microorganism is selected from the group *Trichoderma harizianum* and *Trichoderma reesez*.

13. The method of producing N-acetyl-D-glucosamine according to claim 1, wherein the degradation occurs at a pH of 4.0 to 6.0 and a temperature of 20° to 45° C.

14. The method according to claim 1, or 10, further comprising separating N-acetyl-D-glucosamine from the reaction.

15. The method according to claim 1, or 10, wherein the fungal biomass is derived from citric acid fermentation.

* * * * *